United States Patent [19]

Wright et al.

[11] 4,184,484

[45] Jan. 22, 1980

[54] BODY FLUID PRESSURE INDICATOR AND REGULATOR AND METHOD FOR CONTINUOUSLY REGULATING AND MONITORING THE PRESSURE OF A BODY FLUID

[75] Inventors: Ballard D. Wright, 983 Edgewater, Lexington, Ky. 40502; Susan E. Clifford, Bala Cynwyd, Pa.

[73] Assignee: Ballard D. Wright, Lexington, Ky.

[21] Appl. No.: 841,253

[22] Filed: Oct. 11, 1977

[51] Int. Cl.$^2$ ............................................... A61B 5/00
[52] U.S. Cl. .................................................. 128/748
[58] Field of Search .......... 128/2 F, 2 G, 2 R, 2.05 D

[56] References Cited

U.S. PATENT DOCUMENTS

| | | | |
|---|---|---|---|
| 3,242,920 | 3/1966 | Andersen | 128/2.05 D |
| 3,362,400 | 1/1968 | DeBella | 128/2 F |
| 3,730,168 | 5/1973 | McWhorter | 128/2.05 D |

Primary Examiner—William E. Kamm
Attorney, Agent, or Firm—Frank C. Leach, Jr.

[57] ABSTRACT

Apparatus and method are disclosed for indicating and regulating the pressure of a selected body fluid such as an intracranial fluid. An elongated indicator tube is carried at least in part in a vented chamber which can be mounted so that the indicator tube is in a substantially vertical position. A flexible conduit conveys the selected body fluid from a catheter in the patient to the lower end of the indicator tube. By positioning the indicator tube so that the lower end is level with the in-dwelling end of the catheter, the extent of travel of the body fluid along the tube is a direct indication of the pressure of the body fluid. To provide an upper limit on the pressure the body fluid may attain, at least one opening is provided at a selected position in the wall of the indicator tube inside the chamber. This opening provides an upper pressure limit by permitting fluid to escape from the indicator tube into the chamber when the pressure is sufficient to cause the fluid to reach the opening. The chamber is vented so that compressed air inside the chamber does not affect the fluid pressure reading, and the extent of travel of the fluid inside the indicator tube represents the true pressure of the body fluid. Drainage means is provided for draining the chamber of any body fluid forced thereinto and the flexible conduit has an access port between the indicator tube and the catheter for sampling fluid or for injecting medicament.

15 Claims, 1 Drawing Figure

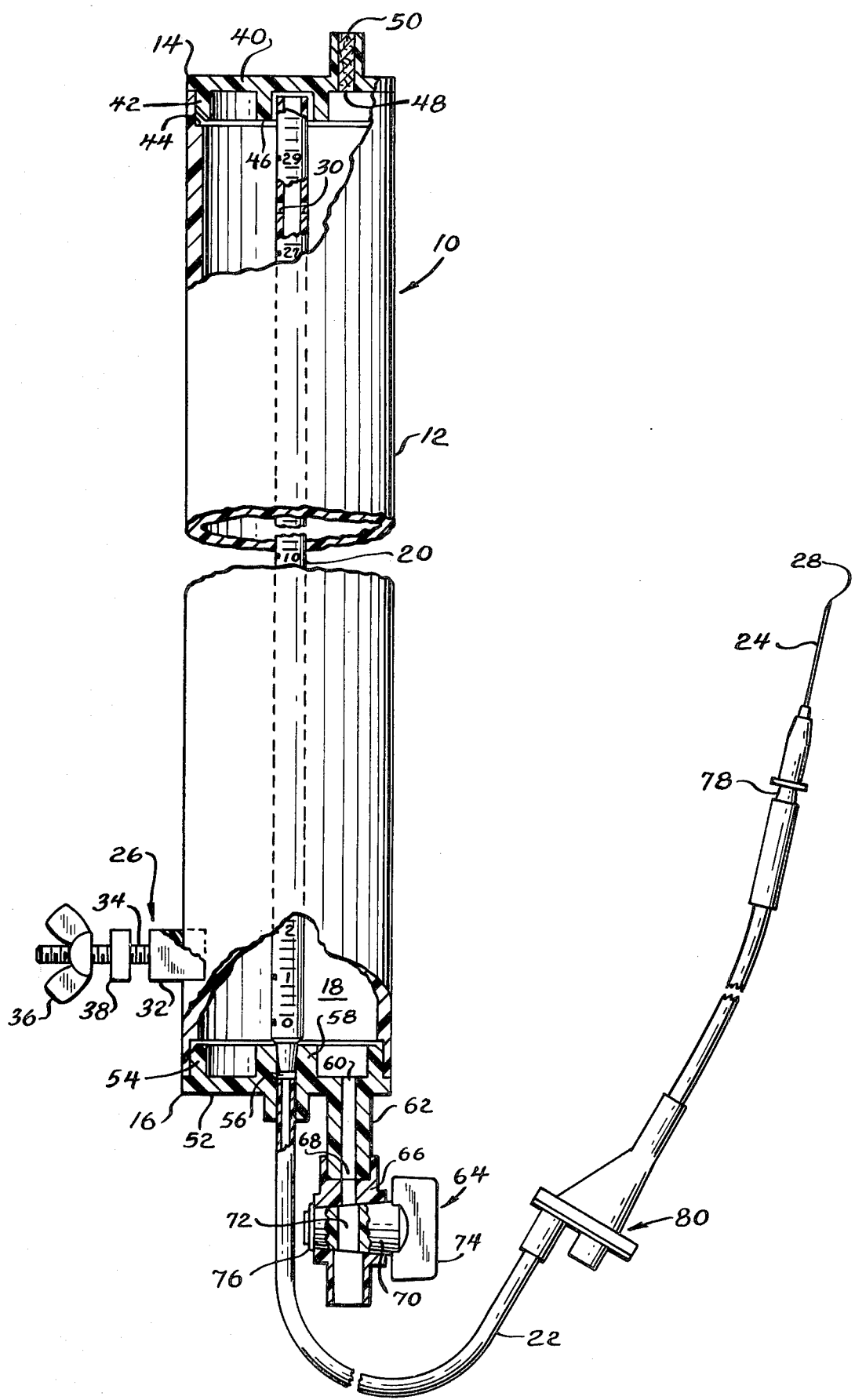

BODY FLUID PRESSURE INDICATOR AND REGULATOR AND METHOD FOR CONTINUOUSLY REGULATING AND MONITORING THE PRESSURE OF A BODY FLUID

The present invention relates to medical apparatus for indicating and regulating the pressure of a select body fluid and a method for continuously regulating and monitoring the pressure of the body fluid. More particularly, the present invention is directed to a continuous pressure indicator and regulator for intracranial fluid and a method for continuously regulating and monitoring the pressure of the intracranial fluid.

The use of instruments for monitoring the pressure of a selected body fluid and the use of catheters for relieving pressure by draining fluid from the body are well known in the medical profession. Typically, the monitoring device informs the physician when excessive fluid pressure occurs. At that point, the physician must decide whether drainage of the body fluid is needed, and if so, how much should be drained to relieve the pressure. For example, with intracranial fluid, the pressure may increase because of tumor, head injury or a variety of other conditions which cause the formation of excessive intracranial fluid.

In cases involving concern about intracranial fluid pressure, the monitoring devices have often utilized complex electronic sensors or transducers implanted in the skull. The output of these sensors is usually an electronic waveform which is displayed on a cathode ray tube. If the waveform indicates a pressure increase, a decision must then be made as to whether to operate to relieve the pressure of the intracranial fluid. And upon operation, a further decision is required by the surgical team as to how much fluid should be drained to relieve the pressure but without collapsing the ventricles of the brain.

With a system which simply displays an electronic signal representative of the pressure of a selected body fluid, it is difficult, and often impractical, to either monitor for or take action to relieve transient pressure increases. And even for a sustained pressure increase, difficult judgments must be made as to the safe amount of fluid that may be withdrawn without adverse physical effects. Because of the necessity for human intervention to relieve pressure increases, apparatus used in the systems above are more properly termed simple pressure monitors, since there is no regulating function. Two examples of this type of intracranial pressure monitors may be found in U.S. Pat. Nos. 4,014,319 and 4,026,276.

Mechanical devices which have been concerned with body fluid pressure have also usually been in the nature of pressure monitors, and have often not been capable of providing an upper limit on the pressure of the fluid. In addition, many of these devices use capilliary tubes or manometers which communicate with a closed chamber so that the compression of air by the body fluid helps balance off the pressure of the body fluid and must be taken into account for an accurate determination of the fluid pressure. Furthermore, many of the older mechanical apparatuses were relatively complicated and could not easily be made in a sterile, disposable configuration. Examples of apparatuses of different design from the present invention may be found in U.S. Pat. Nos. 3,730,168; 3,062,202; 3,920,002; 3,435,819; 3,669,094; 3,526,218; 2,866,453; 2,396,351; and 3,183,722.

Referring specifically to U.S. Pat. No. 3,730,168, a manometer is disclosed which is particularly useful in measuring spinal fluid pressure. The manometer communicates with a closed chamber so that compression of air in the chamber helps balance against the fluid pressure, and therefore must be taken into account in determining the exact fluid pressure. Typical of spinal fluid measuring apparatus, the needle is attached directly to the manometer so that the manometer is positioned locally at the point of needle puncture.

The venous pressure monitoring apparatus in U.S. Pat. No. 3,435,819 is simply a pressure indicator with a float which rises to close a top vent to prevent the escape of fluid from the manometer. Thus, it is specifically designed to prevent pressure relief.

Another device which has been advertised for use in indicating and regulating body fluid pressure utilizes a tube from an intracranial catheter to the top of an apparently closed bag which is hung above the patient. A tape measure is provided to measure the height of fluid in the tubing. Not only is such a system very awkward to use, but because the system is closed, the height alone may not be an accurate measure of the fluid pressure.

Accordingly, it is the general object of the present invention to provide a body fluid pressure indicator and regulator which does not suffer from the shortcomings described above.

It is a further object of the present invention to provide a simple, disposable pressure indicator and regulator which provides an easy-to-read, true indication of body fluid pressure and provides a continuous upper limit for body fluid pressure, even for transient pressure increases. It is another object of the present invention to provide a method for continuously regulating and monitoring the pressure of a body fluid.

These and other objects are met by the present invention by providing an elongated indicator tube, at least a portion of which is mounted in a vented chamber through which that portion of the tube is viewable. The chamber may be mounted so that the indicator tube is in a substantially vertical position, and the lower end of the indicator tube is connected to a source of body fluid so that the extent of travel along the tube indicates the true pressure of the body fluid. To prevent the fluid pressure within the body from exceeding a pre-selected amount, a pressure limiting opening is provided at a selected location along the indicator tube within the chamber. Fluid reaching the limiting opening is channelled from the tube and dumped into the chamber.

In a preferred embodiment, the pressure indicator and regulator is constructed as a compact disposable package. An elongated chamber is provided by a hollow, transparent, plastic barrel which is closed at the top end by a vented plastic cap and at the bottom end by a plastic cap having a center port. An indicator tube in the form of a manometer is mounted inside the barrel with the lower end communicating with the port in the bottom cap. Plastic flexible tubing outside the barrel extends from the central port in the lower cap to a catheter provided for insertion into the patient. After the catheter is inserted, the body fluid is directed along the tubing and into the bottom of the manometer. The barrel is preferably mounted with the bottom of the manometer tube level with the fluid-receiving end of the catheter, so that the vertical travel of body fluid in the manometer tube represents the pressure of the body fluid. To control the pressure of the body fluid and prevent even transient pressure increases above a desired amount, at least one pressure limiting opening is provided in the wall of the indicator tube within the chamber. Body fluid reaching the pressure opening is permitted to escape into the chamber, thereby providing an upper limit to the pressure that the body fluid may obtain, represented by the distance between the bottom of the manometer tube and the pressure limiting opening. This construction provides a continuous monitor and automatic regulator of the body fluid pressure without the need for sophisticated electronic or mechanical apparatus. Pressure increases, whether sustained or transient, are automatically prevented, without the need for human monitoring or intervention. Only a one time decision is required to determine the desired maximum fluid pressure. An indicator and regulator made in accordance with the present invention, with the opening in the manometer at a location corresponding to the desired maximum pressure, is then attached to the patient for continuous monitoring and regulation of the particular body fluid.

These and other objects are shown in the following detailed description and in the attached drawing which is an elevated view, partially in section, of a body fluid pressure indicator and regulator embodying the present invention.

The present invention is generally embodied in a disposable pressure indicator and regulator generally referred to by the numeral 10, which may be easily fabricated in a sterilized condition, for one-time use only. In accordance with the present invention, a hollow transparent barrel 12 is closed at each end by top and bottom end caps, 14 and 16, respectively, to form a generally closed internal chamber 18. An elongated indicator tube in the form of a manometer tube 20 is carried inside the chamber between the end caps and communicates through the lower end cap 16 with flexible tubing 22 which is attached at a distal end to a catheter 24 for insertion into the patient. The barrel 12 has attachment means 26 for mounting the barrel 12 in a substantially vertical position, preferably with the lower end of the manometer tube 20 level with the fluid receiving end 28 of the catheter. Body fluid is then conducted through the tubing 22 and into the manometer tube 20, with the vertical distance the fluid travels along the manometer tube 20 representing the pressure of the body fluid. At least one pressure limiting opening 30 is provided at a selected position along the manometer tube 20 which corresponds to the desired maximum pressure for the fluid. Body fluid exceeding the desired pressure will overflow into the space between the manometer tube 20 and the inside of the barrel 12.

Turning now to a more detailed description of the attached drawing which shows the preferred embodiment of the present invention for purposes of illustration and not limitation, the barrel 12 is of generally cylindrical shape and is preferably fully transparent. It may be constructed of glass, but clear, rigid, non-toxic plastic, is preferred because it is strong, easy to work with and of relatively low cost. For mounting the barrel 12 in a substantially vertical position the mounting means 26 includes a saddle 32 which is attached to the surface of the barrel 12 and at least one threaded bolt 34 extending from the saddle 32 for receiving a wing nut 36 and washer 38 for mounting the barrel 12 to a suitable rigid support (not shown).

The barrel 12 is closed at the top by the vented cap 14, which has a circular top plate portion 40 with a peripheral depending flange 42 of appropriate size to fit snugly against the inside surface of the barrel 12. As shown in the drawing, the inside surface of the barrel 12 at the end may be machined slightly to form a seat 44 for the flange 42 of the cap 14. The cap 14 further has a center annular depending flange 46 which provides a center guide or slot for receiving the upper end of the manometer tube 20. The cap 14 has a vent port 48 which communicates between the outside of the cap 14 and the inside chamber 18, and a suitable microporous filter 50 mounted in the port 48 to provide a sterile barrier against the entry of harmful bacteria or other contaminating matter into the chamber 18. Except for the filter 50, the vented cap 14 is preferably of one-piece, integral plastic construction and may be attached to the barrel 12 by solvent or by high frequency sonic welding.

The barrel 12 is closed at the lower end by the bottom end cap 16 which is mounted in a manner similar to that described for the top cap 14. The bottom cap 16 has a flat circular portion 52 with a peripheral upstanding flange 54 of the appropriate size to snugly fit inside the barrel 12. The cap may be attached to the barrel 12 by solvent or by sonic welding. The bottom cap 16 has a center port 56 extending therethrough and an annular upstanding flange 58 surrounding the port 56 for receiving the lower end of the manometer tube 20, which is tapered for compressively fitting into the annular flange 58.

For draining the barrel 12 of any fluid accumulating between the manometer tube 20 and the inside surface of the barrel 12, a drainage opening 60 is provided in the flat circular plate 52 between the annular center flange 58 and the peripheral flange 54. Extending downwardly from the plate 52 is a short extension or a nipple 62 through which the drainage opening 60 extends.

To control drainage through the drainage opening 60, a plastic petcock 64 is mounted on the end of the extension 62. The petcock 64 has a body portion 66 attached, as by adhesive, to the end of the extension 62. A center bore 68 in the body 66 is aligned with the drainage opening 60, and a tapered valve member 70 with a passageway 72 is mounted in the body 66 for rotation into and out of alignment with the center bore 68, thereby either permitting or preventing flow through the valve body 66. The valve member 70 has a handle 74 for rotating the valve member 70 between the opened and closed positions. When the valve member 70 is in its closed position, the contact between the valve member 70 and the valve body 66 is sufficiently tight to prevent the ingress of bacteria or other harmful micro-organisms into the barrel 12. The valve member 70 is actually held in the valve body 66 by a heat deformed flange 76 on the end opposite the handle 74.

The manometer tube 20 is mounted between the end caps 14 and 16 of the barrel 12. The manometer tube 20 is preferably of cylindrical plastic construction and is graduated for easy reading. The lower end of the manometer tube 20 is tapered for wedging tightly into the center flange 58 of the bottom cap 16. If a satisfactory fluid tight seal is not obtained by simple wedging, solvent or adhesive may be used to secure the end of the manometer tube 20 to the bottom flange 58 of the bottom cap 16. The upper end of the manometer tube 20 may be simply inserted into the guide defined by the center depending flange 46 of the top cap 14, or the upper end of the manometer tube 20 may be sealed into the cap 14, provided sufficient spacing is allowed for venting of air through the top of the manometer tube 20 into the chamber 18. With the preferred construction, the axis of the manometer tube 20 is parallel to the axis at the barrel 12, and in the illustrated embodiment, the manometer tube 20 is concentrically mounted within the barrel 12.

For providing an upper limit to the pressure of the selected body fluid, at least one and preferably two of the openings 30 are provided in the manometer tube 20 at a selected location above the lower end of the tube 20 and within the chamber 18. The openings 30 are positioned corresponding to the desired maximum pressure of the body fluid, so that fluid reaching the openings 30 cannot continue higher in the manometer tube 20, but rather overflows through the openings 30 into the space between the manometer tube 20 and barrel 12. Thus, a maximum or upper pressure limit is maintained. In the illustrated embodiment, the two openings 30 are at the same level, but on opposite sides of the manometer tube 20.

When manufactured in sterile condition, for one-time use only, it may be preferred to have a selection of pressure indicators and regulators available with the openings 30 at different locations, analogous to a glove available in various sizes. With such a selection, a doctor need only select the unit having the predetermined maximum pressure setting desired. For intracranial pressure regulators used with patients suffering from various brain traumas, it has been found that limiting the openings 30 at about 28 cm above the lower end of the manometer tube 20 have provided relief from excessive pressure while providing sufficient pressure to prevent ventricular collapse.

To convey the selected body fluid to the manometer tube 20, the flexible plastic tubing 22 extends from the underside of the bore 56 in the bottom cap 16 to the catheter 24 which is inserted into the cavity containing the body fluid. The plastic tubing 22 is solvent sealed to the surface of the bore 56 and is of sufficient length so that the barrel 12 need not be located immediately adjacent to the patient. The particular type of the catheter 24 used may vary depending on the body fluid being monitored, but it will usually be of flexible plastic or rubber construction so as not to dislodge or cause injury with slight movement of the patient. The tubing 22 may terminate with a "Luer" type plug 78 for insertion into the selected catheter 24.

For either sampling the fluid being monitored or for injecting medicament, an access port 80 is mounted in the tubing 22 intermediate of the bottom cap 16 and the catheter 24. The access port 80 may be of the ordinary Y-type which has three ports, two open ports for entry and exit of body fluid and a third sealed port pierceable, e.g., by a needle, for sampling or for injecting medicine into the fluid. However, the access port 80 is preferably constructed in the manner described in pending U.S. patent application Ser. No. 706,363, filed July 19, 1976, the contents of which are incorporated by reference herein.

It can be seen from the description above that in accordance with the present invention a compact, inexpensive, and disposable device is provided for indicating as well as regulating the pressure of a selected body fluid. A manometer tube is attached directly to a source of body fluid and is mounted in a substantially vertical position so that the travel of fluid in the manometer tube represents the pressure of the body fluid. At least a portion, and preferably the entire manometer tube is enclosed in a surrounding chamber. The manometer tube has pressure limiting openings at a position selected to correspond to the desired maximum fluid pressure. This opening is provided inside the chamber. When body fluid pressure tries to exceed the desired limit, the excess fluid overflows through the openings into the chamber. Since the chamber is vented, the vertical height of liquid in the manometer tube represents the true pressure of the fluid. The entire unit is of almost all plastic construction and may be easily constructed as a pre-sterilized unit for one-time use only. A sampling port is also provided between the body fluid source and the manometer tube for either sampling the fluid being monitored or for injecting medicine. The present invention has been described in terms of the preferred embodiment for purposes of illustration only and not limitation. It is intended that the present invention also cover any of various changes which may be made, some of which may be immediately obvious and other of which may be recognized only after some study, and which come within the following claims.

That which is claimed is:

1. A body fluid pressure indicator and regulator comprising: walls defining an internal chamber, vent opening means in said chamber to continuously vent said chamber to the ambient so that said chamber is always at ambient pressure while maintaining said chamber contamination free, elongated indicator means carried at least in part within said chamber, conveying means for continuously conveying body fluid between its source in the body of a patient and said indicator means without any valve means through said indicator means having its lower end communicating continuously with said conveying means so that the body fluid is conducted into said indicator means when the pressure of the body fluid increases and out of said indicator means when the pressure of the body fluid decreases and is below a maximum desired pressure, the distance the body fluid extends along said indicator means representing the pressure of said fluid, said indicator means having its upper end terminating in said chamber, and said indicator means having pressure limiting opening means interior of said chamber and spaced a selected, fixed distance above said lower end of said indicator means in accordance with the maximum desired pressure of the body fluid, said pressure limiting opening means providing an upper limit to the body fluid pressure by permitting escape of the fluid from said indicator means into said chamber when the pressure of the body fluid exceeds its maximum desired pressure to regulate the pressure of the body fluid.

2. A body fluid pressure indicator and regulator in accordance with claim 1 in which said conveying means comprises a flexible tube, body communicating means to communicate with the source of body fluid in the patient to receive the body fluid, and one end of said flexible tube communicating with said lower end of said indicator means and the other end of said flexible tube communicating with said body communicating means.

3. A body fluid pressure indicator and regulator in accordance with claim 2 in which access port means is provided intermediate of said ends of said tube.

4. A body fluid pressure indicator and regulator in accordance with claim 1 which includes drainage opening means in said chamber for draining body fluid therefrom, and drain valve means carried by said drainage opening means for controlling the flow of fluid therethrough.

5. A body fluid pressure indicator and regulator in accordance with claim 1 which includes sterile barrier filter means in cooperative association with said vent opening means for restricting the admission of harmful material into said chamber.

6. A body fluid pressure indicator and regulator comprising: housing means including both a hollow transparent barrel disposable in a substantially vertically extending position and closure means closing upper and lower ends of said barrel, vent opening means in said housing means located above the lower end of said barrel and communicating with the interior thereof to continuously vent the inside of said barrel to the ambient so that the inside of said barrel is always at ambient pressure, filter means cooperatively associated with said vent opening means to restrict admission of harmful matter into said barrel so that the inside of said barrel is contamination free, a transparent elongated indicator tube carried at least in part in said barrel and being generally parallel thereto for disposition in a substantially vertical position, means for continuously conveying body fluid between the lower end of said indicator tube and a patient without any valve means whereby body fluid is conducted directly into said indicator tube when the pressure of the fluid in the body increases with the vertical distance the fluid extends therealong indicating the pressure of the fluid and the body fluid is returned to the body from said indicator tube when the pressure of the fluid in the body decreases and is below a maximum desired pressure, the upper end of said indicator tube terminating within said barrel at a level above the lower end of said barrel, and pressure limit opening means in the portion of said indicator tube located within said barrel at a selected, fixed distance in accordance with the maximum desired pressure of the body fluid, said pressure limit opening means providing an upper limit to fluid pressure of the body fluid by permitting the body fluid to flow from said indicator tube into the area between said indicator tube and the inside of said barrel if said fluid reaches said pressure limit opening means due to the pressure of the body fluid exceeding its maximum desired pressure.

7. An indicator and regulator in accordance with claim 6 in which calibration means is provided along said indicator tube for indicating the pressure of said fluid.

8. An indicator and regulator in accordance with claim 6 in which the closure means closing the lower end of said barrel includes a drain opening means communicating between said indicator tube and the inside of said barrel and valve means resistant to the transmission of bacteria carried by said drain opening means for controlling the flow of fluid therefrom.

9. An indicator and regulator in accordance with claim 6 in which said conveying means comprising a flexible tube communicating at one end with the lower end of said indicator tube and communicable at the other end with the patient.

10. An indicator and regulator in accordance with claim 9 in which said flexible tube includes an access port intermediate of said ends of said flexible tube.

11. An intracranial fluid pressure indicator and regulator comprising:
a hollow transparent barrel,
mounting means associated with said barrel for mounting in a vertical position,
upper and lower end caps closing each end of said barrel,
vent opening means in said upper cap for continuously venting the inside of said barrel to the ambient to maintain the inside of said barrel at ambient pressure,
filter means carried on said upper cap adjacent said vent opening means to restrict admission of harmful matter into said barrel through said vent opening means to maintain the inside of said barrel contamination free,
fluid opening means in said lower end cap for receiving body fluid,
an elongated, transparent indicator tube completely enclosed within said barrel and extending generally parallel to the axis of said barrel, said indicator tube having its lower end supported by said lower end cap,
body communicating means insertable into a patient,
a fluid conveying tube exterior of said barrel terminating at one end of said fluid opening means in said lower cap and terminating at the other end with said body communicating means, said flexible tubing having a fluid access port between said ends thereof,
the lower end of said indicator tube continuously communicating with said fluid opening means in said lower cap so that intracranial fluid may be continuously communicated between the patient and said indicator tube with the fluid flowing into said indicator tube when the pressure of the fluid in the patient increases and returning to the patient from said indicator tube when the pressure of the fluid in the patient decreases and is below a maximum desired pressure, the vertical travel of the fluid in said indicator tube representing the pressure of the intracranial fluid of the patient,
drain valve means in said lower cap communicating between said indicator tube and the inside of said barrel for selectively draining fluid from between said indicator tube and the inside of said barrel while preventing contamination of the inside of said barrel,
and pressure limiting opening means in said indicator tube spaced a selected, fixed distance from the lower end of said indicator tube in accordance with the maximum desired pressure of the intracranial fluid whereby the intracranial fluid reaching said pressure limiting opening means will flow into the space between said indicator tube and the inside of said barrel to relieve the pressure of the intracranial fluid until it decreases to the maximum desired pressure so that the pressure of the intracranial fluid is regulated.

12. The intracranial fluid pressure indicator and regulator of claim 11 in which:
said indicator tube has its upper end supported by said upper end cap,
and said pressure limiting opening means comprises at least one opening located at a selected distance above the lower end of said indicator tube in accordance with the maximum desired pressure of the intracranial fluid, said opening being below the upper end of said indicator tube.

13. A method of continuously regulating and monitoring the pressure of a body fluid of a patient including:
providing communication without any valve means between a source of body fluid in a patient and an elongated indicator means having a relatively small constant cross sectional area in its portion in which the pressure of the body fluid is indicated so as to be monitored and disposed at least partially within a contamination free chamber;

continuously maintaining the chamber at ambient pressure;

disposing the elongated indicator means relative to the source of the body fluid so that the level of the body fluid in the elongated indicator means continuously indicates the pressure of the body fluid in the patient whereby the pressure of the body fluid can be continuously monitored until it reaches a maximum desired pressure;

regulating the pressure of the body fluid in the patient through relieving the pressure of the body fluid in the patient when it exceeds the maximum desired pressure by channelling fluid due to the pressure of the body fluid exceeding the maximum desired pressure from the elongated indicator means into the chamber until the pressure of the body fluid does not exceed the maximum desired pressure;

and allowing the return of body fluid to the patient only from the elongated indicator means when the pressure of the body fluid decreases and the pressure is below the maximum desired pressure.

14. The method according to claim 13 including disposing the elongated indicator means in a substantially vertical position.

15. The method according to claim 14 including draining the body fluid from the chamber without causing any contamination of the chamber and prior to the level of the body fluid in the chamber reaching a level at which it can flow into the elongated indicator means.

* * * * *

UNITED STATES PATENT AND TRADEMARK OFFICE
CERTIFICATE OF CORRECTION

PATENT NO. : 4,184,484
DATED : April 5, 1980
INVENTOR(S) : Ballard D. Wright et al It is certified that error appears in the above—identified patent and that said Letters Patent is hereby corrected as shown below:

IN THE ABSTRACT

Line 3, "an" should read -- as --.

Column 2, line 35, the sentence beginning with "It" should be the start of a new paragraph.

Column 7, line 57, "comprising" should read -- comprises --.

Signed and Sealed this

Twenty-fourth Day of June 1980

[SEAL]

Attest:

SIDNEY A. DIAMOND

Attesting Officer     Commissioner of Patents and Trademarks